(12) United States Patent
Yan et al.

(10) Patent No.: US 8,883,228 B2
(45) Date of Patent: Nov. 11, 2014

(54) COMPOSITION FOR HEART DISEASE, ITS ACTIVE INGREDIENTS, METHOD TO PREPARE SAME AND USES THEREOF

(75) Inventors: Xijun Yan, Tianjin (CN); Naifeng Wu, Tianjin (CN); Zhixin Guo, Tianjin (CN); Zhengliang Ye, Tianjin (CN); Yan Liu, Tianjin (CN)

(73) Assignee: Tasly Pharmaceutical Group Co. Ltd., Tianjin (CN)

( * ) Notice: Subject to any disclaimer, the term of this patent is extended or adjusted under 35 U.S.C. 154(b) by 1108 days.

(21) Appl. No.: 12/706,522

(22) Filed: Feb. 16, 2010

(65) Prior Publication Data

US 2010/0136146 A1 Jun. 3, 2010

Related U.S. Application Data

(63) Continuation of application No. 10/903,110, filed on Jul. 30, 2004, now abandoned.

(60) Provisional application No. 60/491,466, filed on Jul. 31, 2003.

(51) Int. Cl.
A61K 36/258 (2006.01)
A61K 36/537 (2006.01)
A61K 31/045 (2006.01)
A61P 9/10 (2006.01)

(52) U.S. Cl.
USPC ........... 424/728; 424/746; 424/464; 514/16.4

(58) Field of Classification Search
None
See application file for complete search history.

(56) References Cited

U.S. PATENT DOCUMENTS

| | | |
|---|---|---|
| 4,755,504 A | 7/1988 | Liu |
| 4,999,343 A | 3/1991 | Liu |
| 5,288,485 A | 2/1994 | Kikuta et al. |
| 5,401,502 A | 3/1995 | Wunderlich et al. |
| 5,433,957 A | 7/1995 | Kikuta et al. |
| 5,589,182 A | 12/1996 | Tashiro et al. |
| 5,776,463 A | 7/1998 | Arginteanu |
| 7,396,545 B2 | 7/2008 | Cheng et al. |
| 8,486,464 B2 | 7/2013 | Yan et al. |
| 2003/0152651 A1 | 8/2003 | Yan et al. |
| 2005/0037094 A1 | 2/2005 | Yan et al. |

FOREIGN PATENT DOCUMENTS

| | | |
|---|---|---|
| CN | 1100657 A | 3/1995 |
| CN | 1101556 A | 4/1995 |
| CN | 1185963 A | 7/1998 |
| CN | 1041494 C | 1/1999 |
| CN | 1249943 A | 4/2000 |
| CN | 1055630 C | 8/2000 |
| CN | 1325725 A | 12/2001 |
| CN | 1348815 A | 5/2002 |
| CN | 1919240 A | 2/2007 |
| CN | 1919248 A | 2/2007 |
| CN | 101181350 A | 5/2008 |
| DE | 1467767 A | 12/1968 |
| EP | 0 009 728 A1 | 4/1980 |
| JP | 6-211713 A | 8/1994 |
| JP | 2003-088323 A | 3/2003 |
| KR | 20010018271 A | 3/2001 |
| KR | 20020028041 A | 4/2002 |
| WO | WO 02/058625 A2 | 8/2002 |
| WO | WO 02058625 A2 * | 8/2002 |

OTHER PUBLICATIONS

Anonymous: Internet Article, "Dan Shen Pill", XP002262543, "URL:http://www.carbotrading.com/Products/Medicine/JZ016. htm" Nov. 18, 2003.
Anonymous: Internet Article, "Dan Shen Tablet", XP002262544, "URL:http://www.craneherb.com/Products/product001513>" Nov. 18, 2003.
www.dalian-info.com, p. 1-3, cited on Oct. 22, 2003 in Office Action for Taiwan Application No. 90,132,075, filed Dec. 21, 2001, Attachment 1.
Cai, P.Y. et al. A clinical study of Hehuantang in treating coronary heart disease. Chin J Integr Med, 16(4): 204-6 (1996). English abstract on p. 204.
Chang, Y.Z. et al. Protective effect of DS-182 on the H+—ATPase activity of rat myocardial mitochondria against free radical damage. Chin J of Path, 7(5): 449-52 (1991). English abstract on p. 452.
Chen, K. et al. Clinical study on the effect of Shuxuening tablet in treatment of coronary heart disease. Zhongguo Zhong Xi Yi Jie He Za Zhi (Chinese Journal of Modem Developments in Traditional Medicine), 16(1):24-6 (1996). English abstract on p. 24.
Chen, T.F. et al. Enhancement of absorption of tetramethylpyrazine by synthetic borneol. Acta Pharmacol Sin, 11(1): 42-44 (1990). English abstract on p. 42.
Chen, Z.H. et al. Studies on effects of "Danshensu" on experimental microcirculatory disturbances and plasma lactic acid concentrations. Acta Acad Med Shanghai, 14(1):25-29 (1987). English abstract on p. 29.
Cheng, Y.Y. et al. Effect of *Silvia miltiorrhiza* on the cardial ischemia in rats induced by ligation. Chin J Integr Med, 12: 390, 424-6 (1992). English abstract on p. 390.
Chinese Drugs of Plant Origin, 749-750 (1992); cited in the Apr. 30, 2005 Office Action for Korean Application No. 10-2003-7008308, filed Jun. 20, 2003, corresponding to International application No. PCT/US01/49396, filed Dec. 18, 2001.
Chinese Drugs of Plant Origin, 898-899 (1992); cited in the Apr. 30, 2005 Office Action for Korean Application No. 10-2003-7008308, filed Jun. 20, 2003, corresponding to International application No. PCT/US01/49396, filed Dec. 18, 2001.

(Continued)

*Primary Examiner* — Michele C. Flood

(74) *Attorney, Agent, or Firm* — Finnegan, Henderson, Farabow, Garrett & Dunner, LLP

(57) ABSTRACT

This invention provides a composition for heart disease comprising extracts from raw herbs of 80.0-97.0% Radix *Salviae Miltorrhizae*, 1.0-19.0% *Panax Notoginseng* and 0.1-1.0% Borneol and its active ingredients. This invention also provides a method for preparing said composition and the active ingredients of the composition. Finally, this invention provides various uses of said compositions and the active ingredients.

5 Claims, No Drawings

(56) References Cited

OTHER PUBLICATIONS

European Search Report for Tianjin Tasly Pharmaceutical Co., Ltd., China, European Appl. No. EP 03 017260.5, Filed Jul. 30, 2003. Dated Dec. 5, 2003.
Fang, K.-H., et al. Study on the preparation of potassium antimony tartrate pills by the drop method. Yaoxue Xuebao (1958), 6: 380-4. English abstract only.
Guan, M. et al. Observations on the treatment of coronary heart disease by kuo guan qu yu ling. J Tradit Chin Med., 10(1):49-53 (1990).
Han, C. et al. The protective effects of redix *Salviae miltiorrhizae* on the ischemic and post-ischemic reperfusion injury of the heart. Chin J of Path, 7(4): 337-41 (1991). English abstract on p. 340.
He, W. et al. Effects of kuo guan powder on immunologic functions in patients with ben-xu biao-shi syndrome in ischemic heart disease. Zhongguo Zhong Xi Yi Jie He Za Zhi (Chinese Journal of Modern Developments in Traditional Medicine), 9(4):213-5 (1989).
Hu, J.X. et al. Clinical and experimental study of Shenshao Tongguan Pian in treating angina pectoris of CHD (coronary heart disease). Zhongguo Zhong Xi Yi Jie He Za Zhi (Chinese Journal of Modern Developments in Traditional Medicine), 10(10): 580, 596-9 (1990). English abstract on p. 580.
Hu, Y.J. et al. Effects of artificial cultured *Panax notoginseng* on cardiovascular system. Chin J Chin Mater Med, 17(6):361-3, 384 (1992). English abstract on p. 384.
Huang, C. et al. Effects of *Panax notoginseng* Saponins on myocardial ischemia and reperfusion injury in conscious rabbit. Chin Bull Pharmacol, 7: 190-3 (1991).
Hungarian Novelty Search Report for Tianjin Tasly Pharmaceutical Co., Ltd., China, Hungarian Application No. 0331720, filed Jul. 22, 2003. Dated Feb. 28, 2005.
International Search Report for WO 02/058625 A3, for Tianjin Tasly Pharmaceutical Co., Ltd., China; "Herbal Composition for Angina Pectoris, Method to Prepare Same and Uses Thereof" Published Aug. 1, 2002.
Jiang, W. et al. (W.T. Chiang) et al. Effects of "Danshensu" and other two water-soluble components of *Salvia miltiorrhiza* on dog ischemic myocardium and isolated pig coronary artery. Acta Aced Med Prim Shanghai, 9: 13-19 (1982). English abstract on p. 19.
Jiang, W. et al. Some pharmacologic effects on the "styrax pill for coronary dieasse" and the pharmacological basis of a simplified styrax-bomeol preparation. Acta Pharmaceutica Sin, 14(11): 665-61 (1979). English abstract on p. 661.
Jiang, H.W. et al. Clinical study in treating Qi-deficiency and blood-stasis syndrome of angina pectoris with Qi Xue granule. Chin J Integr Med, 12(11): 644, 663-5 (1992). English abstract on p. 644.
Jin, C. et al. Effect of *Astragalus membranaceus* on erythrocyte sodium content and sodium transport in the coronary heart disease. Zhongguo Zhong Xi Yi Jie He Za Zhi (Chinese Journal of Modern Developments in Traditional Medicine), 11(11): 643, 651-3 (1991). English abstract on p. 643.
Lei, Z.Y. et al. Action of *Astragalus membranaceus* on left ventricular function of angina pectoris. Chin J. Integr Med, 14(4): 195, 199-202 (1994). English abstract on p. 195.
Li, C.Z. et al. Experimental studies on the mechanism of inhibition from thrombus formation by *Silviae miltiorrhizae* bunge in vitro. Acta Acad Med Prim Shanghai, 6:145-50 (1979). English abstract on p. 150.
Li, C.Z. et al. Experimental study on the Anticoagulative action of Danshensu. Zhongguo Zhong Xi Yi Jie He Za Zhi (Chinese Journal of Modern Developments in Traditional Medicine), 3: 260, 297-9 (1983). English abstract on p. 260.
Li, H.T. and Shi, L. Effects of total saponins of *Panax notoginseng* on $Ca^{2+}$ influx into myocardial cells. Acta Pharmacol Sin, 11(3): 213-7 (1990). English abstract on p. 213.
Li, R. et al., Qunatitative Determination of Total Tanshinone in *Salvia miltiorrhiza* Tablet Compound, Yiyao Gongye—Pharmaceutical Industry, Shanghai, CN; vol. 17, No. 11 1986, pp. 513-514, XP002954785. English abstract on p. 514.

Li, S.Q. et al. Clinical observation on treatment of ischemic heart disease with *Astragalus menbranaceus* Integr Med, 15(2):77-80 (1995). English abstract on p. 77.
Li, X. et al. Protective effects of *Panax notoginseng* saponins on experimental myocardial injury induced by ischemia and reperfusion in rat. Acta Pharmacol Sin, 11(1): 26-29 (1990). English abstract on p. 26.
Li, Y. et al. Effects of Kuo-guan granule on plasma zinc, copper and erythrocyte GSH-Px (glutathione peroxidase) in patients with angina pectoris. Zhongguo Zhong Xi Yi Jie He Za Zhi (Chinese Journal of Modem Developments in Traditional Medicine), 10(6): 325, 348-50 (1990). English abstract on p. 325.
Li, Y.Y. Clinical and experimental studies on the effect of Xue Mai Tong on coronary heart disease. Zhongguo Zhong Xi Yi Jie He Za Zhi (Chinese Journal of Modem Developments in Traditional Medicine), 9(2): 68, 79-81 (1989). English abstract on p. 68.
Lin, Q.C. A clinical study of Guan Mai Le in the treatment of coronary heart disease. Zhongguo Zhong Xi Yi Jie He Za Zhi (Chinese Journal of Modern Developments in Traditional Medicine), 9(5): 251, 280-2 (1989). English abstract on p. 251.
Liu, K.Y. et al. Clinical observation on treatment on treatment of 45 angina pectoris patients of coronary heart disease with Taponin. Zhongguo Zhong Xi Yi Jie He Za Zhi (Chinese Journal of Modem Developments in Traditional Medicine), 15(11): 649-51 (1995). English abstract on p. 649.
Liu, Y. et al., Evaluation of Radix *Salviae miltiorrhizae* and its Preparation. Chinese Materia Medica, Mar. 1999;15(3): 159-162. Medline Database Accession No. NLM2085402, XP002262545. English Abstract only.
Lu, B.J. et al. Effect of Sheng Mai San on lipid peroxidation in acute myocardial infarction patients. Chin J lntegr Med, 14(12): 712-4 (1994). English abstract on p. 712.
Luo, Xiao-jian et al. A Brief Account of the Study on Fufangdashen Tablets. Chinese Traditional Patent Medicine. vol. 23, No. 5, May 2001, pp. 371-373. English abstract on p. 371.
Medical Study Material at the Middle Level, p. 1-7, Oct. 1995, cited on Oct. 22, 2003 in Office Action for Taiwan Application No. 90,132,075, filed Dec. 21, 2001, Attachment 2.
Mo, Q.X. et al. Dynamics of 3H-Bomeol. Propriet Trad Chin Med Res, 8: 5-7 (1982).
Ni, K. et al., Determination of Active Components of *Salvia miltiorrhiza* and Notoginseng in Compound *Salvia miltiorrhiza* Tablets by TLC—Densitometry, Yaowu Fenxi Zazhi—Chinese Journal of Pharmaceutical Analysis, Zhongguo Yaoxuehui, Beijing, CN, vol. 9, No. 2, 1989, pp. 74-77, XP002954784. English abstract on p. 77.
Pan, J.G. et al. Chemical Studies on Essential Oils from Six *Artemisia* Species. Chin J Chin Mater Med, 17: 741-46, 764 (1992). English abstract on p. 764.
Pan, X. et al., Inhibitory effects of total saponins extracted for *Panax ginseng, Panax quinquefolium* and *Panax notoginseng* on platelet function and thrombosis in rats. Zhongguo Yaolixue Yu Dulixue Zazhi, 7(2): 141-144 (1993). English abstract only.
PCT International Search Report for Yan, et al, Int'l, Application No. PCT/1B03/03774, Filed Jul. 31, 2002, Dated Dec. 15, 2003.
Preliminary Amendment filed Jul. 30, 2004 in U.S. Appl. No. 10/903,110.
Shi et al. Quality Analysis at Dan Shen Pian. p. 1-18, www.cpha.org.cn, cited on Oct. 22, 2003 in Office Action for Taiwan Application No. 90,132,075, filed Dec. 21, 2001, Attachment 3.
Shi, L. et al. Effects of total saponins of *Panax notoginseng* on increasing $PGI_2$ in carotid artery and decreasing $TXA_2$ in blood platelets. Acta Pharmcol Sin, 11(1): 29-32 (1990). English abstract on p. 29.
Singaporean Search Report and Written Opinion for Tianjin Tasly Pharmaceutical Co., Ltd., China, Singaporean Application No. 200304274-4, Filed Jul. 31, 2003. Dated Mar. 24, 2005.
STN Search Results, (Jun. 2005), U.S. Appl. No. 10/210,548.
Sun, X.M. et al. Studies on a new pharmacological action of an extract of Den-shen (*Salvia miltiorrhiza*). Chin Med Herb, 22: 20-23, 48 (1991). English abstract on p. 48.

(56) References Cited

OTHER PUBLICATIONS

Sun, Yikun et al. Study on the Standard Specification and Investigation on Quality of Compound Danshen Tablet. Chinese Pharmaceutical Patent Affair, vol. 14, No. 6, Jun. 2000, pp. 383-385. English abstract on p. 383.

Supplementary Partial European Search Report for Tianjin Tasly Pharmaceutical Co., Ltd., China, European Application No. EP01994322, Filed Jul. 4, 2003. Dated Jul. 22, 2004.

The State Pharmacopoeia Commission of P.R. China, comp. Fufang Danshen Pian. Pharmacopoeia of the People's Republic of China. English Edition 2000. vol. 1, 280-81.

Wang, B. et al. Clinical observation on 406 cases of angina pectoris in coronary heart disease treated with saponin of *Tribulus terrestris*. Zhongguo Zhong Xi Yi Jie He Za Zhi (Chinese Journal of Modern Developments in Traditional Medicine), 10(2): 68, 85-7 (1990). English abstract on p. 68.

Wang, N.S. et al. Experimental studies of Benefits of Borneol as an Assistant or a guide. J Trad Chin Med 35: 46-7 (1994).

Wang, S. et al. Effects of Codonopsis pilosulae on the synthesis of thromboxane A2 and prostacyclin. Zhongguo Zhong Xi Yi Jie He Za Zhi (Chinese Journal of Modern Developments in Traditional Medicine), 10(7): 387, 391-4 (1990). English abstract on p. 387.

Wang, X.F. et al. Clinical observation of Wenxin decoction in treating 82 patients with spontaneous angina pectoris. Chin J Integr Med, 16(4): 201-3 (1996). English abstract on p. 201.

Wolff, H. L. Apoth. Ztg. (1930), 45: 22-4. Preparation of stable digitalis pills. Abstract.

Wu, H.Z. et al. In vitro inhibitory effect of 764-3 on human platelet aggregation and release reaction, Chin J of Hematology, 15(9):458-60, 500-501 (1994). English abstract on p. 500.

Wu, Y. et al. Clinical study on Xintongkang capsule in treating angina pectoris of coronary heart disease. Zhongguo Zhong Xi Yi Jie He Za Zhi (Chinese Journal of Modern Developments in Traditional Medicine), 10(7): 387, 395-8 (1990). English abstract on p. 387.

Wu, Y.Z. et al. On mechanism of effects of Radix Silviae Miltiorrhizae in promoting blood circulation and removing blood stasis. Acta Nanjing Univ Trad Chin Mater Med, 11: 35-6, 64 (1995). English abstract on p. 64.

Wu, Y.Z. et al. An assessment of Radix Silviae Miltiorrhizae in promoting blood circulation by removing blood stasis. Acta Nanjing Univ Trad Chin Mater Med, 11: 35-6 (1995).

Xing, Z.Q. et al. Effect of *Salvia miltiorrhiza* on serum lipid peroxide, superoxide dismutase of the patients with coronary heart disease. Chin J Integr Med, 16(5):287-9 (1996). English abstract on p. 297.

Xu, Q. et al. Studies on blood-lipid decreasing action of total saponins of *Panax notoginseng*. (Burk.) F.H. Chen. Chin J Chin Mater Med, 18(6): 367-8, 383 (1992). English abstract on p. 383.

Xu, W. and Wang Z.R. Effect of menthol and borneol on the distribution of suffadiazine sodium and Evan's blue in the rat and mouse brain. Pharmacol Chin Med Clin, 6: 31-33 (1995). English abstract on p. 33.

Yang, G.Y. and Wang, Wei. Clinical studies on treatment of coronary heart disease with *Valeriana officinalis var latifolia*. Chin J Integr Med, 14(9): 540-2 (1994). English abstract on p. 540.

Yiwu et al. Corydalis Yanhusuo. p. 1-5 (1999), cited on Oct. 22, 2003 in Office Action for Taiwan Application No. 90,132,075, filed Dec. 21, 2001, Attachment 4.

Yuan, J-P. et al. J. Agric. Food Chem. 1998, 46, 2651-2654. Simultaneous Determination of Rosmarinic Acid, Lithospermic Add B, and Related Phenolics in *Salvia miltiorrhiza* by HPLC.

Zhang, H. et al. Clinical study on effects of buyang huanwu decoction on coronary heart disease. Chin J Integr Med, 15(4): 213-5 (1995). English abstract on p. 213.

Zhang, X.L. et al. Preliminary exploration on Rose Shu-Xin oral liquid in treating angina pectoris of CHD. Chin J Integr Med, 12 (7): 389, 414-6 (1992). English abstract on p. 389.

Zhou, W. et al. Protective effect of danshen during myocardial ischemia and reperfusion: an isolated rat heart study. Am J Clin Med, 18(1-2):19-24 (1990).

Zhu, H.G. et al. Clinical study on xinkening in treating asymptomatic myocardial ischemia in coronary heart disease. Chin J Integr Med, 14(4): 196, 213-5 (1994). English abstract on p. 196.

\* cited by examiner

COMPOSITION FOR HEART DISEASE, ITS ACTIVE INGREDIENTS, METHOD TO PREPARE SAME AND USES THEREOF

CROSS REFERENCE TO RELATED APPLICATIONS

This application is a continuation of U.S. application Ser. No. 10/903,110, filed on Jul. 30, 2004 now abandoned, which claims benefit of priority to U.S. Provisional Application No. 60/491,466, Filed Jul. 31, 2003, the content of U.S. application Ser. No. 10/903,110 and U.S. Provisional Application No. 60/491,466 are hereby incorporated in their entireties for all of their teachings by reference into this application.

Throughout this application, various publications are referenced and full citations for these publications may be found in the text where they are referenced. Disclosures of these publications in their entireties are hereby incorporated by reference into this application to more fully describe the state of the art to which this invention pertains.

BACKGROUND OF THE INVENTION

Heart disease includes a number of conditions affecting the structure or function of the heart. They can include: coronary artery disease, including heart attack, abnormal heart rhythms, heart failure, heart valve disease, congenital heart disease, heart muscle disease or cardiomyopathy, and pericardial disease.

Heart disease is the leading cause of death for both men and women in the United States. Treatment of heart disease depends on the type of disease as well as many additional factors. Coronary artery disease is treated with: medications such as aspirin; beta-blockers; nitroglycerin tablets, sprays, and patches; calcium channel blockers; thrombolytic therapy; and surgeries such as coronary angioplasty and coronary bypass operations.

The number of patients with cardiovascular or cerebrovascular disease increases along with higher living standards (better food supply), the worldwide aging problem, and young adults' involvement. It has become the second-most-common disease worldwide threatening the health of human beings.

Angina pectoris is caused by insufficient blood and oxygen supply to the heart. The main clinical symptom is chest pain. It is caused by atherosclerosis or spasms of the coronary artery in about 90% of angina pectoris patients.

The major treatments for angina pectoris are vessel dilation, lowering of blood viscosity, anti-aggregation of platelets and anti-coagulation. The traditional medicines used are nitrates, beta-adrenoceptor blocking drugs and calcium-channel blocking drugs. However, all these drugs have many side effects which make them unsuitable for long-term use. For example, some patients experience a swelling sensation in their heads, rapid heartbeat and even lapse into coma after taking glyceryl trinitrate.

This invention involves a medication which can prevent and cure coronary heart disease with angina pectoris, the methods of manufacture and other usages of the medication. The medication, Dan Shen Pill (DSP), is made from a variety of Chinese herbs using a series of standard procedures.

DSP is an improvement on Dan Shen Tablet (DST) (recorded in Pharmacopoeia of the People's Republic of China Edition, 1977, 1985, 1995, and 2000), but there are significant differences between DSP and DST, specifically, the proportions in their formulas, manufacturing techniques and their clinical results.

Although there are many Chinese herbal medicines used for treating angina pectoris, fewer people use them nowadays. DST or capsules are still being sold in the market, but their manufacturing techniques are old, their efficacy is low and there are no quality control standards. DST is taken orally and absorbed in the gastrointestinal tract, where it is absorbed into blood vessels after processing in the liver. The bioavailability is low, and the absorption speed is low, which is not suitable for the emergency treatment of patients with angina pectoris. Accordingly, DSP is superior to DST.

Throughout this application, various publications are referenced and the disclosures of these publications are hereby incorporated by reference into this application in order to more fully describe the state of art as known to the skilled artisan therein as of the date of invention described and claimed herein.

SUMMARY OF THE INVENTION

This invention provides a composition and its active ingredients for treating heart disease. The heart disease includes chronic stable angina pectoris, coronary artery disease (including heart attack), abnormal heart rhythm, heart failure, heart valve disease, congenital heart disease, heart muscle disease (cardiomyopathy), and pericardial disease. This invention also provides a composition comprising extracts from raw herbs of 80.0-97.0% Radix *Salviae Miltorrhizae*, 1.0-19.0% *Panax Notoginseng* and 0.1-1.0% Borneol.

This invention provides the above composition wherein the extracts are made from raw herbs of 90.0-97.0% Radix *Salviae Miltorrhizae*, 2.5-9.6% *Panax Notoginseng* and 0.2-0.5% Borneol. This invention provides the above composition wherein the extracts are made from raw herbs of 89.8% Radix *Salviae Miltorrhizae*, 9.6% *Panax Notoginseng* and 0.5% Borneol.

This invention provides a method comprising steps of: (1) obtaining an appropriate amount of smashed Radix *Salviae Miltorrhizae* and *Panax Notoginseng*; (2) extracting the obtained Radix *Salviae Miltorrhizae*, and *Panax Notoginseng* in hot aqueous reflux; (3) filtering and combining the extracts to form a combined extract; (4) concentrating the combined extract from step (3) to an appropriate ratio of the volume of the concentrated extract to the weight of the inputted herbal materials to form a concentrated extract; (5) precipitation by organic solvent to form a precipitate; (6) concentrating the supernatant liquid of precipitate resulting from step (5) to form a plaster; (7) mixing the plaster from step (6) with an appropriate amount of Borneol, thereby producing the composition comprising extracts of Radix *Salviae Miltorrhizae*, *Panax Notoginseng* and Borneol for heart disease.

The above composition contains Sodium 3'4-dihydroxyphenyllactate, 3'4-dihydroxyphenyllactate, Protocatechuic Aldehyde, Salvianolic acid A, B, C, D, E, F, Rosemarinic acid, Ginsenoside Rg1, Ginsenoside Rb1, Ginsenoside Re, Notoginsenoside R1, Borneol, etc.

In another embodiment, the above composition further contains methyl tanshinonate, methyl rosmarinate, danshexinkum, lithospermic acid, d-borneol, 1-borneol, tanshinone I, tanshinone IIA, tanshinone IIB, tanshinone V, tanshinone VI, isotanshinone, miltirone, dihydrotanshinone, 1-dehydrotanshinone and neocryptotanshinone, Salvianolic acid G and Salvianolic acid I, lithospermic acid B, ethyl lithospermate, dimethyl lithospermate, monomethyl lithospermate, ginsenoside Rd, ginsenoside Rg2, ginsenoside Rg3, ginsenoside Rh1 and ginsenoside Rh2, notoginsenoside R2, notoginsenoside R3, notoginsenoside R4, notoginsenoside R6, and notoginsenoside R7.

This invention also provides a pill composition capable of treating chronic stable angina pectoris comprising about 0.14 to about 0.18 mg 3'4-dihydroxyphenyllactate per pill, about 6.50 to about 40.50 mg Sanchinoside R1 per pill and about 25.60 to about 86.20 mg Ginsenoside Rg1 per pill.

This invention provides a composition for the treatment of cardiovascular and cerebrovascular disease comprising active ingredients extracted from *Salvia miltiorrhiza* Beg., *Panax notoginseng* or Ginseng, and *Dryobalanops aromatica Geartu.F.* or *Cinnammon camphor* or synthetic borneol. The active ingredient extracted from *Salvia miltiorrhiza* Beg. contains one or more ingredients selected from tanshinone, salvianolic acid, methyl tanshinonate, rosmarinic acid, methyl rosmarinate, danshexinkum, protocatechualdehyde, Sodium 3'4-dihydroxyphenyllactate, and lithospermic acid. The ingredient extracted from *Panax notoginseng* or Ginseng contains one or more ingredients selected from notoginsenoside and ginsenoside. The ingredient extracted from *Dryobalanops aromatica Geartu.F.* or *Cinnammon camphor*. contains d-borneol or l-borneol or both of them.

The said tanshinone includes tanshinone I, tanshinone IIA, tanshinone IIB, tanshinone V, tanshinone VI, isotanshinone, miltirone, dihydrotanshinone, 1-dehydrotanshinone, and neocryptotanshinone. The said salvianolic acid includes Salvianolic acid A, Salvianolic acid B, Salvianolic acid C, Salvianolic acid D, Salvianolic acid E, Salvianolic acid G, and Salvianolic acid I. The said lithospermic acid includes lithospermic acid B, ethyl lithospermate, dimethyl lithospermate, and monomethyl lithospermate. The said ginsenoside includes ginsenoside Rb1, ginsenoside Rd, ginsenoside Re, ginsenoside Rg1, ginsenoside Rg2, ginsenoside Rg3, ginsenoside Rh1, and ginsenoside Rh2. The said notoginsenoside includes notoginsenoside R1, notoginsenoside R2, notoginsenoside-R3, notoginsenoside R4, notoginsenoside R6, and notoginsenoside R7.

This invention provides the above composition comprising Magnesium Salvianolate B or 3'4-dihydroxyphenyllactate extracted from the *Salvia miltiorrhiza* Beg., Ginsenoside $Rb_1$ extracted from the *Panax notoginseng* or Ginseng, and d-Borneol extracted from the *Dryobalanops aromatica Geartu.F.* or *Cinnammon camphor*. In an embodiment, the composition comprises 10-80 mg of Magnesium Salvianolate B, 10-50 mg of Ginsenoside $Rb_1$ and 5-30 mg of Borneol. In a further embodiment, the composition is characterized by comprising 50 mg of Magnesium Salvianolate B, 20 mg of Ginsenoside $Rb_1$ and 15 mg of d-Borneol.

This invention provides the above composition, comprising 5-80 mg of sodium 3'4-dihydroxyphenyllactate, 10-50 mg of Ginsenoside $Rb_1$ and 5-30 mg of Borneol. In a further embodiment, this invention provides the above composition comprising 20 mg of sodium 3'4-dihydroxyphenyllactate, 20 mg of Ginsenoside $Rb_1$ and 15 mg of d-Borneol.

This invention provides the above composition further comprising one or more kinds of excipients, such as polyethylene glycol, xylitol, lactobacillus, starch for preparation of dripping pills, wherein the ratio of weight of the above total extracts or above total pure ingredients to the weight of excipient is 1:1-1:4. For example, 50 mg of Magnesium Salvianolate B, 20 mg of Ginsenoside $Rb_1$, 15 mg of d-Borneol and 265 mg of excipient are contained per ten dripping pills; 20 mg of sodium 3'4-dihydroxyphenyllactate, 20 mg of Ginsenoside $Rb_1$ and 15 mg of d-Borneol and 265 mg of excipient are contained per ten dripping pills.

The Salvianolate B was extracted by steps of: pulverizing *Salvia miltiorrhiza* Beg. into a fine powder, and decocting twice with hot water; combining the decoctions, and concentrating under vacuum at about 50° C.; loading the solution from the step (b) into macroporous adsorption resin and, after washing with water, eluting column with 40% ethanol; After recovering the ethanol from solution obtained in the step (c), refining it by Sephadex LH-20 or other gel columns with the similar characteristics, eluting with ethanol and collecting eluant containing Magnesium Salvianolate B; repeating the process of step (d) until the concentration of Magnesium Salvianolate B reaches more than 90%. The purity of concentration of Magnesium Salvianolate B was assayed by HPLC at a detective wavelength of 281 nm.

The Ginsenoside $Rb_1$ was extracted by steps of: pulverizing *Panax notoginseng* or Ginseng into fine powder, and decocting with water; or refluxing with 70% ethanol; or percolating with 70% ethanol; recovering solvent from the solution at reduced pressure; loading the solution from the step (b) into macroporous adsorption resin, and after washing with water, eluting column with 40% ethanol; After recovering the ethanol from solution obtained in the step (c), refining it by silica gel column; eluting the column with chloroform, methanol and water in the ratio of 6:3:1, respectively, and collecting eluant; Using TLC for examination of Ginsenoside $Rb_1$ and recovering the solvent, thereby obtaining Ginsenoside $Rb_1$.

DETAILED DESCRIPTION OF THE INVENTION

This invention provides a composition for treating heart disease. Heart disease includes chronic stable angina pectoris, coronary artery disease (including heart attack), abnormal heart rhythm, heart failure, heart valve disease, congenital heart disease, heart muscle disease (cardiomyopathy), and pericardial disease.

This invention provides a composition for treatment of heart disease comprising the extract of raw herbs of Radix *Salviae Miltorrhizae, Panax Notoginseng* and Borneol.

This invention also provides a composition comprising herb extracts from raw herbs of 80.0-97.0% Radix *Salviae Miltorrhizae*, 1.0-19.0% *Panax Notoginseng* and 0.1-1.0% Borneol.

This invention provides the above composition wherein the extracts are made from raw herbs of 90.0-97.0% Radix *Salviae Miltorrhizae*, 2.5-9.6% *Panax Notoginseng* and 0.2-0.5% Borneol.

This invention provides the above composition wherein the extracts are made from raw herbs of 89.8% Radix *Salviae Miltorrhizae*, 9.6% *Panax Notoginseng* and 0.5% Borneol.

This invention provides a preparation method comprising steps of: (1) obtaining an appropriate amount of smashed Radix *Salviae Miltorrhizae* and *Panax Notoginseng*; (2) extracting the obtained Radix *Salviae Miltorrhizae* and *Panax Notoginseng* in hot aqueous reflux; (3) filtering and combining the extracts to form a combined extract; (4) concentrating the combined extract from step (3) to an appropriate ratio of the volume of the concentrated extract to the weight of the inputted herbal materials to form a concentrated extract; (5) precipitating by organic solvent to form a precipitate; (6) concentrating the supernatant liquid of precipitate resulting from step (5) to form a plaster; (7) mixing the plaster from step (6) with an appropriate amount of Borneol, thereby producing the composition comprising extracts of Radix *Salviae Miltorrhizae, Panax Notoginseng* and Borneol for heart disease.

In an embodiment, the hot aqueous reflux is at about 60-100° C. In another embodiment, the ratio of the volume of the concentrated extract to the weight of the inputted herbal materials is 1 liter: about 0.7-1.3 kg of herbal material. In a separate embodiment of step (5), ethanol is used for precipitation. In a further embodiment, the concentrated extract from step (5) is added to a final concentration of about 50-85% ethanol. In another embodiment, the plaster is about 1.15-1.45 in relative density.

The above composition contains Sodium 3'4-dihydroxyphenyllactate, 3'4-dihydroxyphenyllactate, Protocatechuic Aldehyde, Salvianolic acid A, B, C, D, E, F, Rosemarinic acid, Ginsenoside Rg1, Ginsenoside Rb1, Ginsenoside Re, Notoginsenoside R1, Borneol, etc.

In another embodiment, the above composition further contains methyl tanshinonate, methyl rosmarinate, danshexinkum, lithospermic acid, d-borneol, 1-borneol, tanshinone I, tanshinone IIA, tanshinone IIB, tanshinone V, tanshinone VI, isotanshinone, miltirone, dihydrotanshinone, 1-dehydrotanshinone and neocryptotanshinone, Salvianolic acid G and Salvianolic acid I, lithospermic acid B, ethyl lithospermate, dimethyl lithospermate, monomethyl lithospermate, ginsenoside Rd, ginsenoside Rg2, ginsenoside Rg3, ginsenoside Rh1 and ginsenoside Rh2, notoginsenoside R2, notoginsenoside R3, notoginsenoside R4, notoginsenoside R6, and notoginsenoside R7.

This invention also provides a pill composition capable of treating chronic stable angina pectoris comprising about 0.14 to about 0.18 mg 3'4-dihydroxyphenyllactate per pill, about 6.50 to about 40.50 mg Sanchinoside R1 per pill and about 25.60 to about 86.20 mg Ginsenoside Rg1 per pill.

This invention provides a composition for treatment of chronic stable angina pectoris, comprising 5-40% water-soluble phenolic acid of Radix Salviae Miltorrhizae, 1-10% water-soluble saponin of Panax Notoginseng and 1-5% of Borneol.

This invention provides the composition comprising 10-30% water-soluble phenolic acid of Radix Salviae Miltorrhizae, 2-6% water-soluble saponin of Panax Notoginseng and 1-3% of Borneol.

This invention provides a composition capable of treating chronic stable angina pectoris and produced eight peaks, when subjected to steps of: (a) Dissolving a suitable amount of said composition in internal standard para-aminobenzonic acid solvent; (b) Using Danshensu and Protocatechuic Aldehyde as the standards; (c) Performing the HPLC assay; and (d) Calculating according to the internal standard method.

This invention provides a composition capable of treating chronic stable angina pectoris comprising about 0.14 to about 0.18 mg Danshensu per pill, more than 12.12 µg Sanchinoside R1 per pill and more than 56.26 µg Ginsenoside Rg1 per pill.

This invention provides the above composition produced by steps of: (a) Extracting Radix Salviae Miltorrhizae, Panax Notoginseng separately in hot aqueous reflux and filtering separately; (b) Concentrating filtrates separately; (c) Refining the concentrates separately using resin columns and concentrating, and getting refined water-soluble extract of Radix Salviae Miltorrhizae and refined water-soluble extract of Panax Notoginseng; and (d) Mixing the refined water-soluble extracts from step (c) with an appropriate amount of borneol, thereby producing a composition capable of treating chronic stable angina pectoris.

This invention provides the above composition produced by steps of:

(1) extraction of water-soluble components of Panax Notoginseng (a) diluting herbs with 5-7 times water; (b) extracting water-soluble components of Panax Notoginseng by boiling in a tank with air pressure between 0.04-0.06 mPa for 2 hours; (c) repeating extraction under the same conditions for 1.5 hours; (d) filtering the extraction with 100-mesh net; (e) refining the filtrate using macroporous adsorption resin eluting with ethanol; and (f) concentrating the eluted extracts under decompressed conditions with the air input to 0.04-0.06 mPa and the vacuum to −0.076~−0.088 mPa until the density is 1.33-1.35;

(2) extraction of water-soluble components of Radix Salviae Miltorrhizae (a) diluting herbs with 5-7 times water; (b) extracting water-soluble components of Radix Salviae Miltorrhizae by boiling in a tank with the air pressure between 0.04-0.06 mPa for 2 hours; (c) repeating extraction under the same condition for 1.5 hours; (d) Filtering the extraction with 100-mesh net; (e) concentrating the filtrates under decompressed conditions with vacuum pressure of −0.076~−0.088 mPa until one Kg initial herb becomes one liter; (f) precipitating the concentrates with ethanol; (g) filtering the ethanol precipitate solution through 100-mesh net; (h) Concentrating the filtrates under decompressed conditions with input air pressure of 0.04-0.06 mPa and vacuum pressure of 0.076~−0.088 mPa; (i) refining the concentrates by polyamide chromatography eluting with ethanol; and (j) concentrating the refined extracts to the density of 1.33-1.35;

(3) producing the pill. (a) mixing the extracts of Panax Notoginseng, the extracts of Radix Salviae Miltorrhizae, synthetic borneol, and polyethylene glycol 6000 at the ratio of 4.0:20.6:1.9:79.5; (b) melting the mixture; (c) manufacturing the melted mixture to pills using a dropping machine with the following characteristics: the temperature of the dropping pot is constantly 89-93° C., the cooling solution is liquid paraffin, of which the temperature is lower than 8° C., the inner diameter of the dropping head is 1.8 mm, the outer diameter of the dropping head is 2.4 mm, the distance between the dropping head and the surface of the cooling solution is 15 cm; and (d) centrifugation of the pills at 800-1100 rpm for 15 minutes to remove oils.

This invention provides the composition for the treatment of chronic stable angina pectoris comprising Sodium 3'4-dihydroxyphenyllactate, Protocatechuic Aldehyde, Salvianolic acid A, B, C, D, E, F, Rosemarinic acid, Ginsenoside Rg1, Ginsenoside Rb1, Ginsenoside Re, Notoginsenoside R1, Borneol, etc.

The herbal composition comprising the above composition should contain 0.14-0.18 mg 3'4-dihydroxyphenyllactate per pill.

This invention provides a composition for the treatment of heart disease comprising pure active ingredients extracted from Salvia miltiorrhiza Beg., Panax notoginseng or Ginseng, and Dryobalanops aromatica Geartu.F. or Cinnamon camphor or synthetic borneol. The active ingredient extracted from Salvia miltiorrhiza Beg. contains one or more ingredients selected from tanshinone, salvianolic acid, methyl tanshinonate, rosmarinic acid, methyl rosmarinate, danshexinkum, protocatechualdehyde, Sodium 3'4-dihydroxyphenyllactate, and lithospermic acid. The ingredient extracted from Panax notoginseng or Ginseng contains one or more ingredients selected from notoginsenoside and ginsenoside. The ingredient extracted from Dryobalanops aromatica Geartu.F. or Cinnamom camphor. contains d-borneol or 1-borneol or both of them.

The said tanshinone includes tanshinone I, tanshinone IIA, tanshinone IIB, tanshinone V, tanshinone VI, isotanshinone, miltirone, dihydrotanshinone, 1-dehydrotanshinone, and neocryptotanshinone. The said salvianolic acid includes Salvianolic acid A, Salvianolic acid B, Salvianolic acid C, Salvianolic acid D, Salvianolic acid E, Salvianolic acid G, and Salvianolic acid I. The said lithospermic acid includes lithospermic acid B, ethyl lithospermate, dimethyl lithospermate, and monomethyl lithospermate. The said ginsenoside includes ginsenoside Rb1, ginsenoside Rd, ginsenoside Re, ginsenoside Rg1, ginsenoside Rg2, ginsenoside Rg3, ginsenoside Rh1, and ginsenoside Rh2. The said notoginsenoside includes notoginsenoside R1, notoginsenoside R2, notoginsenoside-R3, notoginsenoside R4, notoginsenoside R6, and notoginsenoside R7.

This invention provides the above composition comprising Magnesium Salvianolate B or 3'4-dihydroxyphenyllactate extracted from the *Salvia miltiorrhiza* Beg., Ginsenoside $Rb_1$ extracted from the *Panax notoginseng* or Ginseng, and d-Borneol extracted from the *Dryobalanops aromatics Geartu.F.* or *Cinnammon camphor*. In an embodiment, the composition comprises 10-80 mg of Magnesium Salvianolate B, 10-50 mg of Ginsenoside $Rb_1$ and 5-30 mg of Borneol. In a further embodiment, the composition is characterized by comprising 50 mg of Magnesium Salvianolate B, 20 mg of Ginsenoside $Rb_1$ and 15 mg of d-Borneol.

This invention provides the above composition, comprising 5-80 mg of sodium 3'4-dihydroxyphenyllactate, 10-50 mg of Ginsenoside $Rb_1$ and 5-30 mg of Borneol. In a further embodiment, this invention provides the above composition comprising 20 mg of sodium 3'4-dihydroxyphenyllactate, 20 mg of Ginsenoside $Rb_1$ and 15 mg of d-Borneol.

This invention provides the above composition further comprising one or more kinds of excipients, such as polyethylene glycol, xylitol, lactobacillus, and starch for preparation of dripping pills, wherein the ratio of weight of the above total extracts or above total pure ingredients to the weight of excipient is 1:1-1:4. For example, 50 mg of Magnesium Salvianolate B, 20 mg of Ginsenoside $Rb_1$, 15 mg of d-Borneol and 265 mg of excipient are contained per ten dripping pills; 20 mg of sodium 3'4-dihydroxyphenyllactate, 20 mg of Ginsenoside $Rb_1$ and 15 mg of d-Borneol and 265 mg of excipient are contained per ten dripping pills.

The Salvianolate B was extracted by steps of: pulverizing *Salvia miltiorrhiza* Beg. into a fine powder, and decocting twice with hot water; Combining the decoctions, and concentrating under vacuum at about 50° C.; loading the solution from step (b) into macroporous adsorption resin and, after washing with water, eluting column with 40% ethanol; After recovering the ethanol from the solution obtained in step (c), refining it by Sephadex LH-20 or other gel columns with similar characteristics, eluting with ethanol and collecting eluant containing Magnesium Salvianolate B; repeating the process of step (d) until the concentration of Magnesium Salvianolate B reaches more than 90%. The purity of concentration of Magnesium Salvianolate B was assayed by HPLC at a detective wavelength of 281 nm.

The Ginsenoside $Rb_1$ was extracted by steps of: Pulverizing *Panax notoginseng* or Ginseng into fine powder, and decocting with water; or refluxing with 70% ethanol; or percolating with 70% ethanol; recovering solvent from the solution at reduced pressure; loading the solution from step (b) into macroporous adsorption resin and, after washing with water, eluting column with 40% ethanol; After recovering the ethanol from the solution obtained in the step (c), refining it by silica gel column; Eluting the column with chloroform, methanol and water in the ratio of 6:3:1, respectively, and collecting eluant; Using TLC for examination of Ginsenoside $Rb_1$ and recovering the solvent, thereby obtaining Ginsenoside $Rb_1$.

This invention provides the above composition, wherein d-Borneol was extracted from the trunk of *Dryobalanops aromatica Geartu.F.* or the leaves of *Cinnammon camphor*. by means of vapor distillation or supercritical carbon dioxide extraction. In another embodiment, the Borneol is synthetic.

This invention also provides the above compositions, or its ingredients, formulated in a dropping pellet, pill, capsule, granule, tablet, suspension, injection, syrup, tincture, powder, tea, topical solution, nebula, suppository microcapsule, or other pharmaceutically acceptable form.

In other words, this invention provides a pharmaceutical composition comprising the composition or its ingredients described herein and a pharmaceutically acceptable carrier. As known in the art, pharmaceutically acceptable carriers include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, for example, antimicrobials, antioxidants, chelating agents, inert gases and the like.

This invention provides compositions, or its ingredients capable of increasing blood volume in the coronary artery, relaxing the smooth muscles of blood vessels, improving peripheral circulation, raising the oxygen content in veins, or significantly improving the acute myocardial ischemia or myocardial infarction, protecting the cells from damage by hypoxia or anoxia, protecting cells suffering from myocardial ischemia, improving micro-circulation, preventing arrhythmia, platelet aggregation and thrombosis, dissolving fibrin, lowering blood viscosity, adjusting blood cholesterol or preventing atherosclerosis, raising tolerance to hypoxia or anoxia, preventing the oxidation of lipoprotein or removing the harmful free radicals, lowering plasma ET content, significantly improving liver, kidney and pancreas function, preventing the occurrence or development of blood vessel or nerve diseases, enhancing the immune system, regulating vascular nerve balance.

This invention provides the above compositions and/or its ingredients, capable of preventing and treating cardiovascular and cerebrovascular disease, kidney disease, liver disease, pneumonia, lung or heart disease, pancreatitis, diabetes, vertebral disease, optic vessels disease, optic nerve disease, eccentric headache, chronic stomachitis, dizziness, bone disease, altitude sickness, common diseases of the elderly, treating stable angina pectoris, unstable angina pectoris, angina pectoris of the aged, non-symptomatic myocardial ischemia, different types of coronary heart disease or angina pectoris disease, treating arrhythmia, enlargement of the left ventricle, myocarditis, myocardial infarction or cerebral infraction, treating hyperlipidaemia, high blood viscosity syndrome or high blood pressure, treating diseases caused by micro-circulation disorder, treating stroke, cerebral infarction, cerebral bleeding and other cerebral diseases, treating hepatitis B, chronic liver fibrosis, liver fibrosis, active liver cirrosis, liver cirrosis in the remission period during recovery and other related diseases, treating kidney syndrome and its conjunctive diseases, treating diabetes or its conjunctive diseases, treating cyanosis-type optic vessel diseases, such as venal blockage in the retina, central optic artery blockage in the retina, high blood pressure optic atherosclerosis in the retina, diabetic retinopathy, cento-neuropathy, cento-osmotic neuropathy, ischemic neuropathy, optic neuritis or optic nervous dystrophy, treating dizziness caused by cerebral-arterial ischemia, Meniere's disease, coronary heart disease, treating detrimental death of epicondylus medialis, femoral end necrosis, twisted joints, ligament damage, fractures and proliferation of bone cells, treating bronchitis in children, treating hypoxia or anoxia, and treating Alzheimer's Disease.

This invention provides a dropping machine for manufacturing a small-sized medicament comprising any one of the above described compositions, which can be readily dissolved thus readily delivered to organs, comprising the parts of: (a) Dropping pot in which the temperature of the liquid is 60-100° C.; (b) Apparatus which holds liquid paraffin cooling solution of which the temperature is lower than 8° C.; and (c) Dropping head with 1.8 mm inner diameter and 2.35 mm outer diameter which is distanced from the surface of the cooling solution by approximately 15 cm, said dropping head allowing a dropping speed of over 30 pellets per minute.

This invention provides a method of determining the active fractions (ingredients) of any one of the above compositions which are capable of treating and preventing heart diseases, wherein said method comprising the steps of: (a) fractionating pharmaceutical compositions by high performance liquid chromatography (HPLC); (b) comparing the retention time of the fractions of pharmaceutical compositions with the retention time of saponin R1, saponin Rg1, and saponin Re; and (c) determining if pharmaceutical compositions contain fractions of which retention time is equivalent to the retention time of saponin R1, saponin Rg1 and saponin Re.

This invention provides a method of determining the active fractions (ingredients) of any one of the above compositions which are capable of treating and preventing heart disease, comprising the steps of: (a) Fractionating a pharmaceutical composition by thin layer chromatography (TLC); (b) Comparing the position and color of the fractions of pharmaceutical compositions with the position and color of 3,4-dihydroxyphenyl lactic acid and Protocatechuic Aldehyde; and (c) Determining if pharmaceutical compositions contain the fractions with position and color equivalent to the position and color of 3,4-dihydroxyphenyl lactic acid and Protocatechuic Aldehyde.

The invention also provides a method of treatment using the above compositions and its active ingredients for treating a specific disease. Effective amounts of the composition may be determined and administered to a subject suffering from said disease.

The subject invention further provides a method of treating a subject having a disorder, which comprises administering to the subject a therapeutically effective amount of the above composition and its active ingredients to thereby treat the subject. The subject includes a human and other mammals.

The administration of the composition and its active ingredients may be effected or performed using any of the various methods known to those skilled in the art. The route of administration includes but is not limited to administering intravenously, intramuscularly, intraperitoneally, and subcutaneously.

The therapeutically effective amount of the above compositions may be determined by methods well known to those skilled in the art.

Animal Research

1. The Effects of DSP on Dogs with Myocardial Ischemia and Myocardial Infarction Based on changes in myocardial oxygen consumption and biochemical standards, pharmaceutical effects DSP on curing coronary heart disease were investigated. DSP can significantly improve myocardial ischemia and myocardial infarction, raise the blood oxygen level of venous sinuses, inhibit the release of CK and LDH caused by damage to cardiac muscles, lower the activity of blood serum CK and LDH, suppress the activity of blood vessel substances, ET and TXB2, and raise the 6-Keto-PGF1/TXB2 ratio.

2. The Protection of Myocardial Ischemical Reperfusion Injury from Hypoxia in Rats This research stresses the effects of DSP in myocardial ischemical reperfusion injury from hypoxia in rats, especially on the apoptosis of myocardial cells. Results: Myocardial infarction did not occur after 7 hrs of sham operation. Myocardial hypoxia occurred for 1 hr and myocardial infarction occurred sharply after reperfusing for 6 hrs. DSP can reduce the M-IR area and increase the effects with increasing dosage.

3. Propagation of Myocardial Hypoxia in Mice and Effects of Fas/FasL Proteins Under Deoxygenation and Deoxygenation/Re-Oxygenation Conditions Fas gene is an apoptosis-stimulating gene. Its expressed protein product, Fas antigen, is a cell membrane protein. Recently, it was discovered, in experiments on propagation of myocardial hypoxia, that there is a close relationship between the expressed mRNA of Fas gene and myocardial apoptosis. FasL is the ligand of Fas. It is on the surface of transmembrane proteins, which is homologous to the TNF. It can bind to the receptor Fas on the surface of the cell and give out the death signal. The results show DSP can reduce apoptosis by interfering with Fas/FasL expression, protecting the cells from damage by hypoxia and deoxygenation/re-oxygenation.

4. Effects on Lipidemia and Atherosclerosis in Rabbits

The testing showed that DSP can lower TC, TG, LDL-C, VLDL-C concentration, and TC/HDL-C ratio in the blood serum in rabbits. DSP also reduced the thickness of the aortic spot plate and the area of the aortic spot plates. DSP could adjust lipoprotein level and prevent atherosclerosis to a certain extent.

5. Anti-Oxidation and Removal of Free Radicals

By comparing the effect of Diltiazem and the effects of DSP on M-IR and its correlated biochemical markers, MDA and SOD can be observed. The SOD activity of the DSP group increased. There was an obvious difference when compared with the control group (P☐0.01). DSP provides protection from injuries caused by reperfusion of the ischemic area and increases the activity of SOD. MDA is the main catabolic product of the oxidation of fats. It can damage the structure of the cell membrane so seriously that heart and liver tissue are damaged. SOD has an effective action of clearance on superoxide anions. It can regulate the oxidation reaction controlled by free radicals. DSP can increase SOD activity, decrease MDA content, lower the oxidation standard, and reduce the level of damage to the organs.

6. Effects on Cardiac Arrhythmia Caused by Exogenous Free Radicals

Langendorff perfusion device was used to pour ferrous sulfate (0.25 mmol/L)/citrate (1.0 mmol/L) into the Wistar rat's artificial heart. The model of free radicals causing heart rhythm irregularity was replicated to observe the effects of DSP. Exogenous free radicals can increase cardiac arrhythmia up to 100% and atrial cellular lysis up to 43%. 1 mg/L verapamil and 50 mg/L DSP can lower the irregularity percentage to 71.4% and 87.5%. It shows that DSP can prevent cardiac arrhythmia caused by free radicals.

7. Clinical Applications for Acute Pancreatitis in Rats

This experiment uses the acute pancreatitis model with multi-organ malfunction in rats to show the change in the blood plasma endothelins and the clinical applications of DSP. The experiment shows that blood plasma ET content increases significantly in acute pancreatitis with malfunction of multiple organs. Blood plasma ET content decreases significantly after DSP treatment, and treatment can greatly improve liver, kidney and pancreas function.

8. Prevention of Platelet Aggregation and Thrombosis

The increasing of cAMP inhibits the activity of phosphoesterase and epoxidase, and reduces the production of prostaglandin peroxide. It can also activate protease to phosphoesterize the membrane protein, alter the effects of membrane protein composition on platelet aggregation, and control platelet aggregation to prevent thrombosis. DSP can increase blood platelet concentration and plasma camp content in order to prevent thrombosis.

9. Effects of DSP on Blood Vessels and Nerve Lesion in Diabetic Rats

DSP cannot thoroughly protect blood vessels and nerves or prevent the occurrence of blood vessel and nerve lesion in diabetic rats, but it can relieve or reduce its occurrence in the 6 month-diabetic rat, especially in terms of protein in the urine and lesion of blood capillaries of the kidneys and retina. This may be related to the function of DSP, which can increase thrombolysis.

Clinical Research on Dan Shen Pill

1. Treatment of Coronary Heart Disease with DSP (1) Ordinary Treatment of Coronary Heart Disease with DSP After DSP became available in the market in China, a large-scale clinical research project was conducted in China. Although different prescriptions were used in different research projects, all clinical and experimental markers were standardized. The effects of DSP on the treatment of coronary heart disease are much better than that of Dan Shen tablet statistically. The treatment is basically similar to that of Isordil and there is no significant difference between them statistically. DSP works efficiently in small dosages. It is convenient, safe, easily absorbed, and has no side effects.

(2) Pain-Killing Effects of DSP on Coronary Heart Disease Compared with Glyceryl Trinitrate The above experiment shows that the effects of DSP treatment on coronary heart disease are similar to that of glyceryl trinitrate. The results of both ECGs are similar 30 mins after treatment, and the Chinese classification of coronary heart disease does not affect the efficacy of DSP.

(3) Effects of DSP on the Onset of Coronary Heart Disease, Heart Pain Frequency and Volume of Glyceryl Trinitrate Used The results show that DSP can reduce onset frequency and volume of glyceryl trinitrate used. The level and duration of pain improved after a certain period of treatment, and the onset frequency also decreased. This explains why DSP can improve blood flow to the heart in addition to relieving pain.

(4) Improvement of Blood Pressure and Cardiac Function in Patients with Coronary Heart Disease The results prove that DSP can improve cardiac function in patients with coronary heart disease and provide improvements in blood flow.

(5) Effects of DSP on ECGs and Blood Flow in Patients with Coronary Heart Disease No significant differences appeared on ECGs and average exercise testing standards to show improvement from DSP and Isordil (P☐0.05), but the average exercise testing standards in the DSP group were much better before and after treatment (P☐0.01). This test proves that the treatment effects of DSP on coronary heart disease are the same as that of Isordil with no side effects and increase in tolerance. Also, DSP controls irregular blood flow, lowers blood viscosity, reduces the occurrence of atherosclerosis, and prevents thrombosis much better than Isordil and can be the first choice for the treatment of coronary heart disease.

(6) Effects of Long-Term DSP Treatment on Coronary Heart Disease

Long-term DSP results are stable, and there is no antibiotic resistance. Isordil can efficiently lower blood pressure, leading to the activation of endogenous nerve and body fluid system and an increase in blood volume. In addition, Isordil works on sulfur radicals inside the capillary wall, but it would consume sulfur radicals in the long term and reduce treatment effects. DSP is a multi-level, multi-subjected and multi-method medicine which improves cardiac muscle; increases blood volume by blocking the chronic calcium route; stabilizes the myocardial membrane; removes free radials; regulates myocardial cells metabolism; improves blood platelets aggregation; and lowers cholesterol and blood viscosity. Therefore, long-term DSP treatment gives significant treatment effects.

(7) Clinical Research on the Effects of DSP on Unstable-Type Angina.

The experiment shows that DSP can reduce oxygen consumption by cardiac muscles, improve blood flow in coronary arteries, and rebalance the oxygen demand-to-oxygen supply ratio in cardiac muscles.

(8) The Effects of DSP on the Treatment of Exertion-Type Angina

DSP can efficiently relieve pain and increase blood flow to the cardiac muscle. DSP can also reduce oxygen consumption, improve blood flow to the coronary artery, rebalance oxygen demand and oxygen supply, and prevent atherosclerosis. It is the ideal medicine for the prevention or treatment of coronary heart disease, angina and atherosclerosis.

(9) Research on Senior Group Angina

Both DSP and Nifedipine can treat angina caused by coronary heart disease, but the latter has side effects which are not suitable for long-term use. In order to choose suitable drugs for patients with a need for long-term treatment of coronary heart disease, a comparative analysis of DSP and Nifedipine in the treatment of angina caused by coronary heart disease was carried out. DSP is made for angina. It activates blood circulation and relieves pain efficiently. Its effects are long lasting, require only a small dosage and have no side effects. Nifedipine is a short-term-effective calcium antagonist with a short half-life and functional time, so angina may occur during medication. It also has many side effects. Many reports state that long-term treatment with Nifedipine is harmful to coronary arteries. DSP can prevent decreased blood flow to the cardiac muscles and the development of atherosclerosis.

2. Effects on Cardiac Arrhythmia

The treatment effects of DSP on cardiac arrhythmia caused by coronary heart disease are significant. It is also helpful to those patients without heart disease. Its functions are: a) calcification. DSP can reduce intracellular calcium concentration and prevent calcium overloading better than verapamil. b) Stabilizing the cell membrane. DSP can protect cardiac muscle and regulate heart rhythm. c) Removal of free radicals. d) Speeding up energy production and utilization. There is no relationship between chronic irregularity of heart rhythm and the addition of resistance and lack of energy supply.

DSP and Di'ao Xinxuekang can both improve cardiac arrhythmia caused by myocarditis and heart malfunction, but DSP does a better job than Di'ao Xinxuekang. DSP can improve blood flow to the cardiac muscles, section ST and T wave in ECGs. In addition, DSP can also reduce platelet aggregation, and platelet viscosity. The results show that patients who take DSP in the long term enjoy relief from symptoms and low reoccurrence of myocarditis.

3. Reverse Function of DSP on Left Ventricular Hypertrophy (LVH)

The above experiment shows that DSP prevents damage caused by free radicals, prevents atherosclerosis, improves blood circulation, decreases blood viscosity and exterior blood vessel resistance, and regulates compliance of cardiac muscles to reverse LVH.

4. DSP Treatment for High Blood Pressure

The experiment shows that DSP can stop and improve LVH and dilate the left ventricle, which can then lower blood pressure and combat angina.

Besides controlling blood pressure efficiently, other important steps for treating high blood pressure include: increasing the reactivity of insulin, lowering insulin level, and improving ET function in blood vessels. DSP is helpful because it also lowers blood pressure.

5. Treatment of Hyperlipidaemia

This research shows that DSP can significantly lower blood lipoprotein level and improve blood flow, especially by the thinning of IMT after treatment. It explains how this drug can prevent atherosclerosis besides providing the above functions. DSP is safe and effective for older patients with coronary heart disease, angina and high blood viscosity.

6. Treatment for Hyperviscosity Syndrome (HS)

Hyperviscosity Syndrome (HS) is a pathobiological concept, a syndrome caused by one or more blood viscosity factor(s). It can lead to lack of blood supply, hypoxia, blocking, etc. in the heart, brain and kidneys. DSP offers the best results in HS treatment. After the normal 28 days of medication, HS symptoms such as nausea, lack of energy, breath holding, anxiety, etc. related to coronary heart disease, cerebral infraction, and kidney disease disappeared gradually. Blood pressure was lowered, and blood circulation improved. TC, TG, Apo-B dropped, and HDLC and Apo-A1 rose. All levels of hemorheology markers dropped. Renal Blood flow increased, and renal function improved. Urine protein decreased, and cardiac function improved.

7. Treatment for Acute Myocardial Infarction (AMI)

DSP can improve blood circulation by dilating coronary arteries, saving cardiac muscle, minimizing the infarction area, and protecting myocardial cells. Therefore, DSP can protect cardiac muscles in the early stages of AMI. It is a convenient medication with no side effects, which is recommended in the clinical field.

8. Effects on Treatment of Cerebral Infarction

The use of DSP to treat low blood supply to the brain, cerebral infarction and internal bleeding is very efficient.

9. Effects on Blood Micro-Circulation

The experimental results show that DSP can make an improvement in bulbar conjunctiva microcirculation and thrombo-elasticity in patients with coronary heart disease and angina.

10. Effects on Immunity of Red Blood Cells

This experiment uses the blood coagulation method of yeasts sensitized by complement, $C_{3b}$-causing yeast aggregation testing and Enzyme-linked Immunosorbent Assay (ELISA), to test the effects of DSP on the immunosorbent ability of red blood cells, CIC, and SIL-2R in patients with coronary heart disease. The experiment shows that DSP can lower SIL-2R level, strengthen the immune system and the immunosorbent ability of red blood cells.

11. Adjustment of Vegetative Nerve

This test uses "Wenger-Chongzhongchongxion" vegetative nerve balance factor analysis to test the heart rate variation (HRV), that is, the fluctuation in the average heartbeat over a certain period of time or over a long time period in the R-R period. Data, including effects on the sympathetic and para-sympathetic nerves can be calculated, to reflect the regulatory function of the vegetative nervous system. After DSP treatment, the percentage of y>+0.56 dropped significantly (P<0.05), but the drop in the Isordil group before and after treatment was not significant, y>+0.56 (P☐0.05). After DSP treatment, SDNN in R-R increased significantly (P<0.01), and there was no significant difference in the Isordil group before and after treatment (P☐0.05). A decrease in HRV means the sympathetic nerve is excited. It is directly proportional to the symptoms in coronary heart disease and the possibility of sudden death and irregularity of heartbeat. DSP can control over-excitement of the para-sympathetic nerve and regulate the balance in the vegetative nerve.

12. DSP Treatment for Liver Disease

There is significant improvement in the treatment of hepatocirrhosis at the stage of losing compensation when DPS is added as a medication. DSP does not have side effects and is helpful in treating hepatocirrhosis.

13. The Effectiveness of DSP Therapy in Diabetes and Related Complications

Trial results reveal that after 3 months of taking DSP, the 40 patients' nail wall microcirculation test indexes had varying degrees of improvement. Their collective cumulative values decreased. Among the patients, those originally with serious abnormalities now had medium abnormality; those originally with medium abnormality had slight abnormalities. The differences before and after treatment were obvious. DSP has positive healing effects on diabetic end-brush neuritis.

14. The Effectiveness of DSP Therapy on Optical Fundus Vascular Diseases

The cause of retinal vein occlusion is still not very clear. Hypertension, hyperlipidemia, and arteriosclerosis are usually considered as likely causes of retinal vein occlusion. Doctors of traditional Chinese medicine believe that it is caused by stagnant blood flow. DSP can activate blood circulation and relieve congestion, improve microcirculation, relieve hydropsy, and encourage blood absorption. In so doing, it can improve eyesight. DSP can also be used to heal different kinds of optical fundus vascular diseases that are generally termed as Xueyuzheng, such as central retinal artery occlusion, hypertensive retinal arteriosclerosis, diabetic retinal lesion, central plasm optic neuropathy, central permeation optic neuropathy, ischemic optic neuropathy, optic neuritis, atrophy of the optic nerve, etc.

15. DSP's Effect on Hemorheology

In the Observation group, besides fibrinogen, whole blood viscosity, whole blood reduction viscosity, plasma viscosity, hematocrit and Aggregation Index of RBC all decreased. The differences before and after treatment were obvious (P<0.05 or P<0.01). Compared with the Control group, whole blood viscosity, whole blood reduction viscosity, plasma viscosity, and Aggregation Index of RBC had obvious decreases (P<0.05 or P<0.01). After treatment, the Control group shared an obvious change only in the hemagglutilation index (P<0.05 or P<0.01).

16. DSP's Healing Effect on Chronic Pulmonary Heart Disease

The total efficacy rate of treatment group is 95% and that of the control group 76%, the difference of which is statistically significant (P☐0.05). The result revealed that the efficacy of DSP is superior to persantin and that hemorheology in the DSP group has more improvement than that in the persantin group. There was a significant difference in the efficacy of the two groups ($X^2$=4.46 and 4.95, P☐0.05). Treatment group results were better than that of the Control group. There were obvious changes in blood flow in the Treatment group before and after treatment compared with that of the Control group (P☐0.05). The blood viscosity of the control group decreased after treatment, but there was no statistical deviation.

17. Treatment of Adrenal Syndrome

The results show that the complete reversal percentage and total efficacy in the treatment group were 55% and 90%, respectively, which was significantly higher than those in the control group: 27.5% and 65% (P☐0.05). DSP, combined with other medications, can improve treatment results and reduce the percentage of reoccurrence.

18. Treatment of Other Diseases (1) Treatment of bronchitis in children. DSP combined with antibiotics can improve treatment results in infections. The DSP treatment ended fever and rales better than that of the control group. DSP raised the recovery percentage for pneumonia in children and shortened the duration of treatment without significant side effects.

(2) Effects on hemicrania. 58 patients with hemicrania were selected from clinics. The result shows that the efficacy in the treatment group is higher than that of the control group (P☐0.05). DSP can efficiently cure and prevent hemicrania.

(3) Treatment of chronic gastritis. DSP can regulate the function of blood vessels, restrain platelet aggregation, control thrombosis, clear out stagnant blood in the gastric mucosa and cure stomachache caused by chronic gastritis. It can efficiently eliminate the dead parts of the erosive gastric mucinitis, activate megakaryocytes, and stimulate production of new cells to improve the recovery from inflammation.

(4) Treatment of dizziness. The total efficacy in the Treatment group and the Control group were 86% and 87.5%, respectively. No significant abnormality was found. These two groups of drugs can treat fainting efficiently. Therefore, DSP can be a convenient and efficient drug to treat fainting caused by insufficient blood supply to the brain.

(5) Treatment of damaged lateral malleolus joint. DSP can eliminate swelling and stagnant blood, and can kill pain. One active ingredient, borneol, can increase DSP's absorption through the skin and maintain concentrations of the drug at the application site, so it can efficiently and quickly treat damage of the lateral malleolus joint. It is helpful in treating broken bones, bone death and proliferation of bone.

(6) Prevention and treatment of plateau hypoxia. Plateau hypoxia can lead to capillary circulation disorder, causing blood-perfusing insufficiency. Plateau hypoxia also leads to high blood viscosity, increased red blood cell quantity—and red blood cell aggregation, enhanced red blood cell rigidity, increased platelet aggregation, and change in pH value. All the above factors affect blood viscosity and the radius of capillaries. Platelet aggregation can increase resistance in capillaries, leading to blockage. When blood viscosity increases, the radius of capillaries also increases and leads to increased resistance and congestion. There are common properties in the blood flow of people with plateau hypoxia: "concentration" (increased red blood cell pressure), "viscosity" (increased whole blood viscosity), and "aggregation" (increased aggregation of red blood cells). All the above are different at different sea levels and durations. Forementioned pharmaphysiologic and clinical research show that DSP can lower hematocrit, blood sedimentation and blood viscosity, so it is helpful in preventing and treating plateau hypoxia.

(7) Prevention and treatment of Senile dementia. Senile dementia can be classified as Alzheimer's Disease (AD), vascular dementia and combined dementia. After DSP treatment, there is statistically significant improvement in AD and vascular dementia by measurement analysis and Chinese medicine clinical observation ($p<0.05$ or $p<0.01$). DSP is helpful for treating sluggishness, reticence, forgetfulness, fatigue, and ecchymosis at a total efficacy of 40%, and sadness, anger, rashness, and irritation at a total efficacy of 85.7%.

This invention will be better understood from the examples which follow. However, one skilled in the art will readily appreciate that the specific methods and results discussed are merely illustrative of the invention as described more fully in the claims which follow thereafter.

Example 1

41.06 g of Radix *Salviae Miltiorrhizae*, 8.03 g of Radix *Notoginseng* were respectively weighed and ground and then sequentially introduced into an extractor. 5 parts water were added. The mixture was decocted for 2 hours, filtered, and the first filtrate was removed. The residue was added to 4 parts water, decocted for 1 hour, filtered, and then this second filtrate was mixed with the first filtrate. The mixed filtrate was concentrated under decompressed conditions until the solution volume (L) to raw materials weight (Kg) ratio was about 0.9-1.1. 95% ethanol was gradually poured in until the concentration of ethanol was 69-71%. This was settled for 12 hours and filtered. The filtrate, in which ethanol is evaporated, is concentrated to extract of the relative of 1.32-1.40.

The above extract was mixed with 0.46 g of borneol and 18 g of polyethylene glycol 6000. The mixture was heated to 85° C., melted for 30 minutes, and then transferred to a dropping machine at 80° C. The melted mixture was dropped into the liquid paraffin, at a temperature of 7° C. The dropping pills were taken out, and the oil was removed.

The dropping pill is a reddish brown-brownish black sphere with an even size, smooth color, scent, and bitter taste. The weight per pill is 25 mg±15%, and the diameter per pill is 3.34±15% mm.

The above dropping pill contains the following active ingredients: Sodium 3'4-dihydroxyphenyllactate, Protocatechuic Aldehyde, Salvianolic acid A, B, C, D, E, F, Rosemarinic acid, Ginsenoside Rg1, Ginsenoside Rb1, Ginsenoside Re, Notoginsenoside R1, Borneol, etc.

Example 2

31.12 g of Radix *Salviae Miltiorrhizae*, 9.21 g of Radix *Notoginseng*, 0.50 g of borneol and 20 g of polyethylene glycol 6000 were processed according to the extraction and preparation method of Example 1, except for the difference in parameters as follows: the temperature of the dropping machine was 64° C., and the temperature of the liquid paraffin was 0° C.

The dropping pill is a reddish brown-brownish black sphere with an even size, smooth color, distinct scent, and bitter taste. The weight per pill is 25 mg±15%, and the diameter per pill is 3.34±15% mm.

The above dropping pill contains the following 5 active ingredients: Sodium 3'4-dihydroxyphenyllactate, Protocatechuic Aldehyde, Salvianolic acid A, B, C, D, E, F, Rosemarinic acid, Ginsenoside Rg1, Ginsenoside Rb1, Ginsenoside Re, Notoginsenoside R1, Borneol, etc.

Example 3

59.36 g of Radix *Salviae Miltiorrhizae*, 6.38 g of Radix *Notoginseng*, 0.34 g of borneol and 21 of polyethylene glycol 6000 were taken and processed according to the extraction and preparation method of Example 1, except for the difference in parameters as follows: the temperature of the dropping machine was 69° C., and the temperature of polymethyl siloxane as condensation liquid was 4° C.

The dropping pill is a reddish brown-brownish black sphere with an even size, smooth color, distinct scent, and bitter taste. The weight per pill is 25 mg±15%, and the diameter per pill is 3.86±15% mm.

The above dropping pill contains the following active ingredients: Sodium 3'4-dihydroxyphenyllactate, Protocatechuic Aldehyde, Salvianolic acid A, B, C, D, E, F, Rosemarinic acid, Ginsenoside Rg1, Ginsenoside Rb1, Ginsenoside Re, Notoginsenoside R1, Borneol, etc.

Example 4

59.36 g of Radix *Salviae Miltiorrhizae*, 6.38 g of Radix *Notoginseng*, 0.34 g of borneol, 40 g of xylitol and 8 g of starch were processed according to the extraction and preparation method of Example 1, except for the difference in parameters as follows: the temperature of dropping machine was at 69° C., the temperature of polymethyl siloxane as condensation liquid was at 4° C.

The dropping pill is a reddish brown-brownish black sphere with an even size, smooth color, distinct scent, and bitter taste. The weight per pill is 35 mg±15%, and the diameter per pill is 3.86±15% mm.

The above dropping pill contains following active ingredients: Sodium 3'4-dihydroxyphenyllactate, Protocatechuic Aldehyde, Salvianolic acid A, B, C, D, E, F, Rosemarinic acid, Ginsenoside Rg1, Ginsenoside Rb1, Ginsenoside Re, Notoginsenoside R1, Borneol, etc.

Example 5

Extraction of water-soluble saponins of *Panax Notoginseng* Radix *Notoginseng* were weighed and ground, and then introduced into an extractor. 6 parts water was added and decocted for 2 hours with the air pressure between 0.04-0.06 mPa, filtered with 100-mesh net, and the first filtrate was removed. The residue was repeated under the same conditions for 1.5 hours and the second filtrate was removed. Two filtrates were mixed and the filtrate was refined using macroporous adsorption resin eluting with ethanol. The eluate is concentrated under decompressed conditions with the air input to 0.04-0.06 mPa and the vacuum to −0.076~−0.088 mPa until the density was 1.33-1.35, thereby extracting water-soluble saponins of *Panax Notoginseng*.

Example 6

Extraction of Water-Soluble Phenolic Acids of Radix *Salviae Miltorrhizae*

Radix *Salviae Miltorrhizae* were weighed and ground, and then introduced into an extractor. 6 parts water was added decocted for 2 hours with the air pressure between 0.04-0.06 mPa, filtered with 100-mesh net, and the first filtrate is got. The residue is repeated under the same condition for 1.5 hours and the second filtrate is got. Two filtrates are mixed and concentrated under decompressed conditions with the vacuum pressure −0.076~−0.088 mPa until one Kg initial herb becomes one liter. The concentrated solution is precipitated with ethanol and filtered with 100-mesh net. The filtrate is concentrated under decompressed conditions with input air pressure 0.04-0.06 mPa and the vacuum pressure 0.076~−0.088 mPa, and refined by polyamide chromatography eluting with ethanol. The eluate is concentrated under decompressed condition with the air input to 0.04-0.06 mPa and the vacuum to −0.076~−0.088 mPa until the density is 1.33-1.35, thereby extract of water-soluble phenolic acids of Radix *Salviae Miltorrhizae* is got.

Example 7

4.0 g of the extract of water-soluble saponins of *Panax Notoginseng* from Example 5, 20.6 g of the extract of water-soluble phenolic acids of Radix *Salviae Miltorrhizae* from Example and 6, 1.9 g of borneol and 79.5 g of polyethylene glycol 6000 are mixed. The mixture is heated to 89° C., melted for 25 mins, and then transferred to a dropping machine at 80° C. The melted mixture is dropped into the liquid paraffin, at a temperature of 8° C. The dropping pills are taken out and, the oil is removed.

The above dropping pill contains the following ingredients: Sodium 3'4-dihydroxyphenyllactate, Protocatechuic Aldehyde, Salvianolic acid A, B, C, D, E, F, Rosemarinic acid, Ginsenoside Rg1, Ginsenoside Rb1, Ginsenoside Re, Notoginsenoside R1 and Borneol, etc.

Example 8

5.8 g of the extract of water-soluble saponins of *Panax Notoginseng* from Example 5, 50.2 g of the extract of water-soluble phenolic acids of Radix *Salviae Miltorrhizae* from Example 6, 0.8 g of borneol, and 82.4 g of polyethylene glycol 6000 are mixed, and processed according to Example 7.

It has been shown in tests that the above dropping pill contains the following active ingredients: Sodium 3'4-dihydroxyphenyllactate, Protocatechuic Aldehyde, Salvianolic acid A, B, C, D, E, F, Rosemarinic acid, Ginsenoside Rg1, Ginsenoside Rb1, Ginsenoside Re, Notoginsenoside R1, Borneol, etc.

Example 9

50 mg of Magnesium Salvianolate B, 20 mg of Ginsenoside $Rb_1$, 15 mg of d-Borneol and 265 mg of polyethylene glycol 6000 were mixed and processed according to the extraction and preparation method of Example 1, except for the difference in parameters as follows: the temperature of the dropping machine was 64° C., and the temperature of the liquid paraffin was 4° C.

Example 10

80 mg of Magnesium Salvianolate B, 10 mg of Ginsenoside $Rb_1$, 10 mg of d-Borneol and 245 mg of polyethylene glycol 6000 were mixed and processed according to the extraction and preparation method of Example 1, except for the difference in parameters as follows: the temperature of dropping machine was 69° C., and the temperature of the liquid paraffin was 5° C.

Example 11

60 mg of Magnesium Salvianolate B, 25 mg of Ginsenoside $Rb_1$, 8 mg of d-Borneol, 200 g of xylitol and 48 g of starch were mixed, and processed according to the extraction and preparation method of Example 1, except for the difference in parameters as follows: the temperature of the dropping machine was 80° C., and the temperature of polymethyl siloxane as condensation liquid was 4° C.

Example 12

30 mg of sodium 3'4-dihydroxyphenyllactate, 40 mg of Ginsenoside $Rb_1$, 15 mg of d-Borneol, 180 g of lactobacillus and 58 g of starch were mixed and processed according to the extraction and preparation method of Example 1, except for the difference in parameters as follows: the temperature of the dropping machine was 80° C., and the temperature of liquid paraffin was 4° C.

Example 13

50 mg of sodium 3'4-dihydroxyphenyllactate, 30 mg of Ginsenoside $Rb_1$, 10 mg of d-Borneol and 250 g of polyethylene glycol 6000 were mixed and processed according to the extraction and preparation method of Example 1, except for the difference in parameters as follows: the temperature of the dropping machine was 80° C., and the temperature of the liquid paraffin was 4° C.

Example 14

40 mg of sodium 3'4-dihydroxyphenyllactate, 25 mg of Ginsenoside $Rb_1$, 8 mg of d-Borneol, 200 g of lactobacillus and 35 g of starch were mixed and processed according to the extraction and preparation method of Example 1, except for the difference in parameters as follows: the temperature of the dropping machine was 80° C., and the temperature of polymethyl siloxane as condensation liquid was 4° C.

Example 15

25 mg of sodium 3'4-dihydroxyphenyllactate, 45 mg of Ginsenoside $Rb_1$, 12 mg of d-Borneol, 185 g of xylitol and 30 g of starch were mixed and processed according to the extraction and preparation method of Example 1, except for the difference in parameters as follows: the temperature of the dropping machine was 80° C., and the temperature of polymethyl siloxane as condensation liquid was 4° C.

Example 16

20 mg of methyl tanshinonate, 15 mg of ginsenoside Rd, 35 mg of ginsenoside Re, 15 mg of d-Borneol, 245 mg of polyethylene glycol 6000 were mixed and processed according to the extraction and preparation method of Example 1, except for the difference in parameters as follows: the temperature of the dropping machine was 80° C., and the temperature of polymethyl siloxane as condensation liquid was 4° C.

Example 17

10 mg of rosmarinic acid, 15 mg of methyl rosmarinate, 20 mg of tanshinone IIA, 25 mg of ginsenoside Rg2, 15 mg of d-Borneol, 215 g of lactobacillus and 30 g of starch were mixed and processed according to the extraction and preparation method of Example 7, except for the difference in parameters as follows: the temperature of the dropping machine was 82° C., and the temperature of polymethyl siloxane as condensation liquid was 4° C.

Example 18

12 mg of Salvianolic acid C, 15 mg of Salvianolic acid E, 20 mg of ginsenoside Rh1, 15 mg of ginsenoside Rh2, 15 mg of d-Borneol, 210 g of lactobacillus and 30 g of starch were mixed and processed according to the extraction and preparation method of Example 7, except for the difference in parameters as follows: the temperature of the dropping machine was 80° C., and the temperature of polymethyl siloxane as condensation liquid was 4° C.

Example 19

8 mg of Salvianolic acid D, 10 mg of Salvianolic acid G, 15 mg of Salvianolic acid I, 30 mg of ginsenoside Rg3, 15 mg of d-Borneol, 245 mg of polyethylene glycol 6000 were mixed and processed according to the extraction and preparation method of Example 7, except for the difference in parameters as follows: the temperature of the dropping machine was 79° C., and the temperature of the liquid paraffin as condensation liquid was 4° C.

Example 20

8 mg of tanshinone IIB, 15 mg of tanshinone I, 8 mg of dimethyl lithospermate, 15 mg of protocatechualdehyde, 15 mg of notoginsenoside R2, 10 mg of notoginsenoside-R3, 15 mg of d-Borneol, 210 g of lactobacillus and 30 g of starch were mixed and processed according to the extraction and preparation method of Example 7, except for the difference in parameters as follows: the temperature of the dropping machine was 85° C., and the temperature of polymethyl siloxane as condensation liquid was 4° C.

Example 21

8 mg of tanshinone V, 12 mg of isotanshinone, 8 mg of monomethyl lithospermate, 10 mg of notoginsenoside R4, 25 mg of ginsenoside Rg1, 15 mg of l-Borneol, 210 g of xylitol and 30 g of starch were mixed and processed according to the extraction and preparation method of Example 7, except for the difference in parameters as follows: the temperature of the dropping machine was 80° C., and the temperature of polymethyl siloxane as condensation liquid was 4° C.

Example 22

8 mg of tanshinone VI, 5 mg of 1-dehydrotanshinone, 5 mg of neocryptotanshinone, 15 mg of ethyl lithospermate, 10 mg of notoginsenoside R6, 15 mg of Salvianolic acid A, 15 mg of d-Borneol, 245 mg of polyethylene glycol 6000 were mixed and processed according to the extraction and preparation method of Example 7, except for the difference in parameters as follows: the temperature of the dropping machine was 80° C., and the temperature of the liquid paraffin as condensation liquid was 4° C.

Example 23

25 mg of lithospermic acid B, 15 mg of dihydrotanshinone, 40 mg of ginsenoside Rb1, 10 mg of notoginsenoside R7, 15 mg of d-Borneol, 215 g of xylitol and 30 g of starch were mixed and processed according to the extraction and preparation method of Example 7, except for the difference in parameters as follows: the temperature of the dropping machine was 80° C., and the temperature of polymethyl siloxane as condensation liquid was 4° C.

Example 24

Magnesium Salvianolate B was extracted by steps of:
(1) Pulverizing *Salvia miltiorrhiza* Beg. into a fine powder and decocting twice with hot water;
(2) Combining the decoctions and concentrating in vacuum under 50° C.;

(3) Loading the solution from the step (2) into macroporous adsorption resin and, after washing with water, eluting column with 40% ethanol;
(4) After recovering the ethanol from solution obtained in the step (3), refining it by Sephadex LH-20 or other gel columns with similar characteristics, eluting with ethanol and collecting eluant containing Magnesium Salvianolate B.
(5) Repeating the process of step (4) until the concentration of Magnesium Salvianolate B reaches more than 90%.

Example 25

Ginsenoside $Rb_1$ was extracted by steps of:
(1) Pulverizing *Panax notoginseng* or Ginseng into a fine powder, and decocting with water; or refluxing with 70% ethanol; or percolating with 70% ethanol;
(2) Recovering solvent from the solution at reduced pressure;
(3) Loading the solution from step (2) into macroporous adsorption resin and, after washing with water, eluting column with 40% ethanol;
(4) After recovering the ethanol from the solution obtained in step (3), refining it by silica gel column;
(5) Eluting the column with chloroform, methanol and water in the ratio of 6:3:1, respectively, and collecting the eluant;
(6) Using TLC for examination of Ginsenoside $Rb_1$ and recovering the solvent, thereby obtaining Ginsenoside $Rb_1$.

Example 26

6 mg of tanshinone IIA, 10 mg of Salvianolic acid A, 8 mg of lithospermic acid B, 25 mg of ginsenoside-Rg1, 12 mg of d-Borneol, 40 g of microcrystalline cellulose, 0.5 g of talc powder and appropriate amount of 3% polyvidone in ethanol solution were taken and made into tablets according to standard procedures.

Example 27

10 mg of rosmarinic acid, 30 mg of sodium 3'4-dihydroxyphenyllactate, 10 mg of ginsenoside-Rg3, 20 mg of notoginsenoside-R1, 8 mg of d-Borneol, 50 g of gelatin and log of glycerin were taken and made into capsules according common practices.

Example 28

Salvianolic acid A, ethyl lithospermate, ginsenoside-Re, notoginsenoside-R3, 10 mg of d-Borneol, 30 g of magnesium stearate, 15 g of starch and an appropriate amount of 3% polyvidone in ethanol solution were taken and made into granules according to routine procedures.

Example 29

10 mg of lithospermic acid, 20 mg of sodium 3'4-dihydroxyphenyllactate, 20 mg of ginsenoside-Rg3, 8 mg of d-Borneol, 35 g of microcrystalline cellulose, 10 g of starch and an appropriate amount of 3% polyvidone in ethanol solution were taken and made into pills according to routine procedures.

Example 30

60 mg of Salvianolic acid B, 10 mg of sodium 3'4-dihydroxyphenyllactate, 20 mg of Ginsenoside $Rb_1$, 10 mg of d-Borneol, 30 mg of mannitol and 5 mg of antallin and an appropriate amount of water were taken and made into a sterile powder for treating infection according to routine procedures.

What is claimed is:

1. A method of preparing a composition for the treatment of chronic stable angina pectoris comprising the following steps:
(a) separately extracting Radix *Salvia miltiorrhiza* and *Panax notoginseng* herbs in hot aqueous reflux, thereby producing an extract of Radix *Salvia miltiorrhiza* and an extract of *Panax notoginseng*;
(b) separately filtering the extracts of Radix *Salvia miltiorrhiza* and *Panax notoginseng*, thereby producing a filtrate of Radix *Salvia miltiorrhiza* and a filtrate of *Panax notoginseng*;
(c) separately concentrating the filtrates of Radix *Salvia miltiorrhiza* and *Panax notoginseng*, thereby producing a concentrate of Radix *Salvia miltiorrhiza* and a concentrate of *Panax notoginseng*;
(d) separately refining the concentrates of Radix *Salvia miltiorrhiza* and *Panax notoginseng* by eluting the concentrates through a resin column and concentrating the eluted concentrates, thereby producing a refined water-soluble extract of Radix *Salvia miltiorrhiza* and a refined water-soluble extract of *Panax notoginseng*; and
(e) mixing the refined water-soluble extracts of Radix *Salvia miltiorrhiza* and *Panax notoginseng* with borneol, thereby producing a composition for treating chronic stable angina pectoris,
wherein the composition comprises from 5 to 40% water-soluble phenolic acid of Radix *Salvia miltiorrhiza*, from 1 to 10% water-soluble saponin of *Panax notoginseng*, and from 1 to 5% of borneol.

2. The method according to claim 1, wherein (1) for the production of the refined water-soluble extract of *Panax notoginseng*:
(i.) the extracting of *Panax notoginseng* herbs in step (a) comprises diluting the *Panax notoginseng* herbs with 5-7 parts of water and boiling in a tank having an air pressure from 0.04 to 0.06 millipascal (mPa) for 2 hours, and repeating the extraction under the same conditions for 1.5 hours;
(ii.) the filtering of the extract of *Panax notoginseng* in step (b) comprises filtering with 100-mesh net; and
(iii.) the refining of the concentrate of *Panax notoginseng* in step (d) comprises passing the concentrate through an adsorption resin, eluting with ethanol, and concentrating the eluted concentrate under decompressed conditions with an air input from 0.04 to 0.06 mPa and a vacuum from 0.076 to 0.088 mPa until the density of the thereby produced refined water-soluble extract of *Panax notoginseng* is from 1.33 to 1.35; and wherein (2) for the production of the refined water-soluble extract of Radix *Salvia miltiorrhiza*:
(i.) the extracting of Radix *Salvia miltiorrhiza* herbs in step (a) comprises diluting the Radix *Salvia miltiorrhiza* herbs with 5-7 parts of water and boiling in a tank having an air pressure from 0.04 to 0.06 mPa for 2 hours, and repeating the extraction under the same conditions for 1.5 hours;
(ii.) the filtering of the extract of Radix *Salvia miltiorrhiza* in step (b) comprises filtering with 100-mesh net;
(iii.) the concentrating of the filtrate of Radix *Salvia miltiorrhiza* in step (c) comprises concentrating under decompressed conditions with a vacuum pressure of from 0.076 to 0.088 mPa to obtain a concentrate, precipitating the concentrate with ethanol, filtering the ethanol precipitate through a 100-mesh net, and concentrating under decompressed conditions with an input air pressure of from 0.04 to 0.06 mPa and a vacuum pressure of from 0.076 to 0.088 mPa; and (iv.) the refining of the concentrate of Radix *Salvia miltiorrhiza* in step (d) comprises passing the concentrate through a polyamide column, eluting with ethanol, and concentrating the eluted concentrate until the density of the thereby produced refined water-soluble extract of Radix *Salvia miltiorrhiza* is from 1.33 to 1.35;

(3) the mixing of the refined water-soluble extracts of Radix *Salvia miltiorrhiza* and *Panax notoginseng* in step (d) comprises mixing the refined water-soluble extracts of Radix *Salvia miltiorrhiza* and *Panax notoginseng*, borneol, and polyethylene glycol 6000 at a ratio of 4.0:20.6:1.9:79.5; and (4) further comprising the following steps:

(f) melting the composition from step (e);

(g) manufacturing pills from the melted composition from step (f) using a dropping machine, wherein the dropping machine comprises a dropping pot at a temperature ranging from 89 to 93° C., a cooling solution comprising liquid paraffin at a temperature lower than 8° C. and a dropping head having an inner diameter of 1.8 millimeters (mm) and an outer diameter of 2.4 mm; and wherein the distance between the dropping head and the surface of the cooling solution is 15 centimeters (cm); and (h) centrifuging the pills from step (g) at from 800 to 1100 rotations per minute (rpm) for 15 minutes to remove oils.

3. The method according to claim 1, wherein the composition comprises from 10 to 30% water-soluble phenolic acid of Radix *Salvia miltiorrhiza*, from 2 to 6% water-soluble saponin of *Panax notoginseng*, and from 1 to 3% of borneol.

4. The method according to claim 2, wherein the composition comprises from 10 to 30% water-soluble phenolic acid of Radix *Salvia miltiorrhiza*, from 2 to 6% water-soluble saponin of *Panax notoginseng*, and from 1 to 3% of borneol.

5. The method according to claim 4, wherein the composition further comprises from about 0.14 to about 0.18 milligrams (mg) of danshensu per pill, at least 12.12 micrograms (μg) of sanchinoside R1 per pill and at least 56.26 μg of ginsenoside Rg1 per pill.

* * * * *